United States Patent
Perov et al.

(12) 
(10) Patent No.: US 6,329,661 B1
(45) Date of Patent: Dec. 11, 2001

(54) BIOCHIP SCANNER DEVICE

(75) Inventors: Alexander Perov, Troitsk (RU); Alexander I. Belgovskiy, Mayfield Heights, OH (US); Andrei D. Mirzabekov, Darien, IL (US)

(73) Assignee: The University of Chicago, Chicago, IL (US)

( * ) Notice: Subject to any disclaimer, the term of this patent is extended or adjusted under 35 U.S.C. 154(b) by 0 days.

(21) Appl. No.: 09/515,814

(22) Filed: Feb. 29, 2000

(51) Int. Cl.[7] ................................................. G01N 21/64
(52) U.S. Cl. ...................... 250/461.2; 250/459.1
(58) Field of Search ........................... 250/461.2, 461.1, 250/459.1

(56) References Cited

U.S. PATENT DOCUMENTS

| | | | |
|---|---|---|---|
| 4,006,360 | * 2/1977 | Mueller | 250/461.2 |
| 5,061,075 | * 10/1991 | Alfano et al. | 356/417 |
| 5,108,179 | * 4/1992 | Myers | 356/344 |
| 5,418,371 | * 5/1995 | Aslund et al. | 250/458.1 |
| 5,459,325 | 10/1995 | Hueton et al. | . |
| 5,528,050 | 6/1996 | Miller et al. | . |
| 5,631,734 | 5/1997 | Stern et al. | . |
| 5,713,364 | * 2/1998 | DeBaryshe et al. | 128/644 |
| 5,874,219 | * 2/1999 | Rava et al. | 435/6 |
| 6,071,748 | * 6/2000 | Modlin et al. | 436/174 |
| 6,104,945 | * 8/2000 | Modell et al. | 600/473 |
| 6,134,002 | * 10/2000 | Stimpson et al. | 356/326 |
| 6,215,894 | * 4/2001 | Zeleny et al. | 382/133 |

OTHER PUBLICATIONS

DNA analysis and diagnostics on oligonucleotide microhips, by Yershov, G. et al, Proc. Natl. Acad. Sci. USA, vol. 93, pp. 4913–4918, May 1996.

* cited by examiner

*Primary Examiner*—Constantine Hannaher
*Assistant Examiner*—Albert Gagliardi
(74) *Attorney, Agent, or Firm*—Joan Pennington

(57) ABSTRACT

A biochip scanner device used to detect and acquire fluorescence signal data from biological microchips or biochips and method of use are provided. The biochip scanner device includes a laser for emitting a laser beam. A modulator, such as an optical chopper modulates the laser beam. A scanning head receives the modulated laser beam and a scanning mechanics coupled to the scanning head moves the scanning head relative to the biochip. An optical fiber delivers the modulated laser beam to the scanning head. The scanning head collects the fluorescence light from the biochip, launches it into the same optical fiber, which delivers the fluorescence into a photodetector, such as a photodiode. The biochip scanner device is used in a row scanning method to scan selected rows of the biochip with the laser beam size matching the size of the immobilization site.

20 Claims, 5 Drawing Sheets

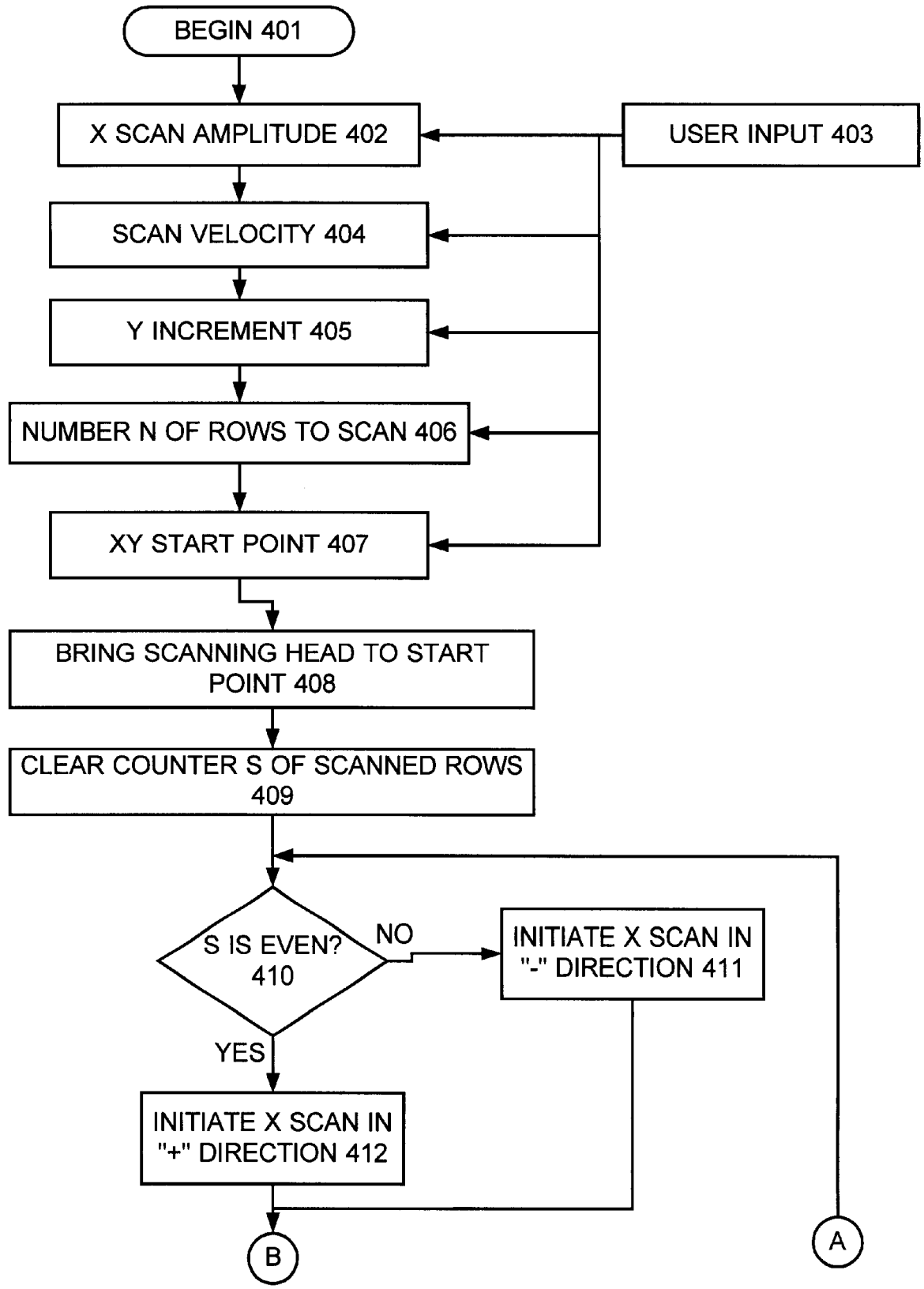

BIOCHIP SCANNER DEVICE

RELATED APPLICATION

A related U.S. patent application Ser. No. 09/515,290 entitled "A PORTABLE BIOCHIP SCANNER DEVICE", by Alexander Perov, Alexei Sharonov and Andrei D. Mirzabekov is being filed on the same day as the present patent application.

CONTRACTUAL ORIGIN OF THE INVENTION

The United States Government has rights in this invention pursuant to Contract No. W-31-109-ENG-38 between the United States Department of Energy (DOE) and the University of Chicago representing Argonne National Laboratory.

FIELD OF THE INVENTION

The present invention relates to a biochip scanner device used to detect and acquire fluorescence signal data from biological microchips (biochips) and method of use.

DESCRIPTION OF THE RELATED ART

At the present time, biochips, after being incubated with a sample solution containing fluorescently labeled target molecules are assayed using either a microscope equipped with a charge coupled device (CCD) camera or a laser scanner. Regardless of the technique of fluorescence measurement used, all known biochip analyzers are high-resolution imaging instruments. This means that their output data is essentially a digital image of the chip composed of approximately 1000N elementary data points, where N represents the number of biochip immobilization sites. As a biochip user is typically interested in relative fluorescence intensities of the immobilization sites, an image as the output data format is highly redundant and requires further processing before the data can be analyzed. This may include signal integration over the immobilization sites, background subtraction, and normalization. The image processing is especially difficult in the case of analyzers based on wide-field microscopes, in which both the sensitivity and the image background are inherently non-uniform.

Due to the restraints on allowable working distance of the objective lens, currently available imaging biochip analyzers cannot be readily used with biochips mounted in an optical flow cell. This feature would be very desirable in order to facilitate the use of an experimental setup designed for multiple biochip use. Further high-resolution imaging requires the use of sophisticated electronic and optical components, which increase the instrument's complexity and cost.

A need exists for an improved mechanism to detect and acquire fluorescence signal data from biological microchips (biochips).

SUMMARY OF THE INVENTION

A principal object of the present invention is to provide a biochip scanner device used to detect and acquire fluorescence signal data from biological microchips (biochips) and method of use. Other important objects of the present invention are to provide such method and biochip scanner device substantially without negative effect; and that overcome some disadvantages of prior art arrangements.

In brief, a biochip scanner device used to detect and acquire fluorescence signal data from biological microchips (biochips) and method of use are provided. The biochip scanner device includes a laser for emitting a laser beam. A modulator, such as an optical chopper modulates the laser beam. A scanning head receives the modulated laser beam and a scanning mechanics coupled to the scanning head moves the scanning head relative to the biochip.

In accordance with features of the invention, an optical fiber delivers the modulated laser light to the scanning head. The scanning head serves for both focusing the excitation laser light onto the biochip and collecting the emitted fluorescence which is then delivered to a photodiode via the same optical fiber. The biochip scanner device is used in a row scanning method to scan selected rows of the biochip with the laser beam size matching the size of the immobilization sites.

BRIEF DESCRIPTION OF THE DRAWINGS

The present invention together with the above and other objects and advantages may best be understood from the following detailed description of the preferred embodiments of the invention illustrated in the drawings, wherein:

FIGS. 4A and 4B together provide a flow chart illustrating a Row Scanning (RS) method of the preferred embodiment.

DETAILED DESCRIPTION OF THE PREFERRED EMBODIMENTS

Figure 1:
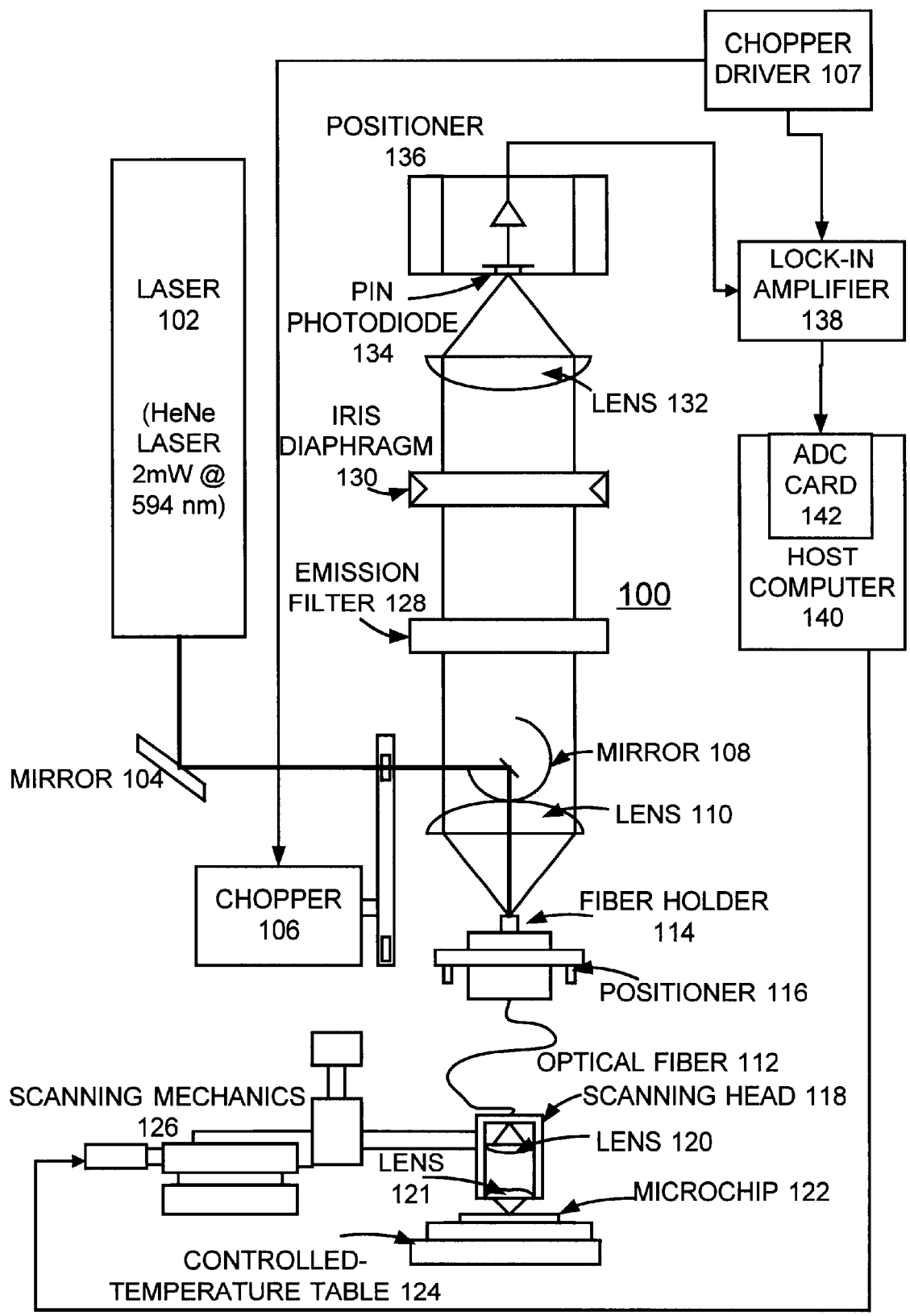
FIG. 1 is a schematic and block diagram illustrating a biochip scanner device in accordance with the preferred embodiment.

Having reference now to the drawings, in FIG. 1, there is shown a biochip scanner device in accordance with the preferred embodiment generally designated by the reference character 100. Biochip scanner device 100 is used to detect and acquire fluorescence signal data from biological microchips (biochips), such as oligonucleotide biochips.

In accordance with features of the invention, biochip scanner device 100 provides advantages over conventional fluorescence microscope equipped with a CCD camera. Biochip scanner device 100 provides much lower and considerably more uniform background. The detector field of view is limited to the focal spot of the laser beam on a microchip surface; as a result, the detector is substantially insensitive to all out-of-focus light. Biochip scanner device 100 provides essentially uniform and reproducible excitation and fluorescence-collection conditions. For each gel pad, the fluorescence is excited and detected under the same conditions; the same detector, the same optical path and the same excitation intensity. Biochip scanner device 100 uses a single-element photodetector that is significantly less expensive than a scientific-grade CCD camera. Biochip scanner device 100 employs a laser, such as a HeNe, diode-pumped solid state, and diode laser, that tend to be more reliable and consume significantly less power than microscopes using high-pressure arc lamps. Biochip scanner device 100 provides an improved data acquisition rate. Biochip scanner device 100 can be used to scan only the chip rows with the beam matching the size of the immobilization site instead of running a high-resolution scan of the entire chip surface. Biochip scanner device 100 allows real-time data processing with the integral signal intensities being available for comparison and storage at the same rate as the rate of the chip being scanned.

Biochip scanner device 100 includes a laser 102 emitting a wavelength matching the excitation band maximum of a particular flurophore. In one embodiment, laser 102 is a 2 mW He—Ne laser emitting at 594 nm, which falls close to the absorption maximum of the popular fluorescent label, "Texas Red". For example, a He—Ne laser model 05 LYR 173 sold by Melles Griot of Irvine, Calif. can be used for laser 102. It should be understood that other lasers could be used for laser 102. The sensitivity of biochip scanner device 100 can be improved by using a red or infrared diode laser 102 as the excitation source. A red or infrared diode laser is more compact and more reliable than a He—Ne laser.

The laser beam is directed by a first mirror 104 and then is modulated by an optical chopper 106. A chopper driver 107 drives the optical chopper 106. In particular, this can be a chopper set at a frequency of 4.3 kHz. It should be understood that other techniques could be used to achieve intensity modulation of the excitation laser light. For example, in the case of a diode laser, the light intensity can be modulated by driving the laser with a periodic train of current pulses with a period corresponding to the desired modulation frequency. A mirror 108 and lens 110 then focus the laser beam into an optical fiber 112 supported by a fiber holder 114 and an X-Y-Z theta-phi positioner 116. The optical fiber delivers the laser beam, excitation light to a miniature scanning head 118. Scanning head 118 contains a first lens 120 and a second objective lens 121. The scanning head 118 is moved relative to a microchip 122.

Examples parts that can be used to form the biochip scanner device 100 are provided in the following; however, it should be understood that various other components could be used. A mirror part number 05D51OBD.1 sold by Newport of Irvine, Calif. can be used for mirror 104. Chopper 106 and chopper driver 107 can be implemented with an optical chopper model 3501 sold by New Focus of Santa Clara, Calif. A mirror part number BRP-5-A sold by Newport of Irvine, Calif. can be used for mirror 108. A lens part number PAC070 sold by Newport of Irvine, Calif. can be used for lens 110. A lens part number PAC510 sold by Newport of Irvine, Calif. can be used for the first lens 120 of the scanning head 118. A lens part number 350340B-00 sold by Geltech of Orlando, Fla. can be used for the objective lens 121 of the scanning head 118. The fiber optic X-Y-Z theta-phi positioner 116 can be implemented with a part number M-FPR2-C1 sold by Newport of Irvine, Calif. An optional fiber patchcord part number F-MCC-T-OPT-10-10 sold by Newport of Irvine, Calif. can be used.

A controlled-temperature table 124 supports the microchip 122. Scanning mechanics 126 is coupled to the scanning head 118 to move the scanning head 118 in both X and Y directions, under computer control, to perform scanning of the biochip 122. A manual stage allows adjustments of the scanning head position in the Z direction perpendicular to the focal plane. Scanning head 118 includes for example, an objective lens 121 with a 3 mm working distance and acceptance angle of approximately 77°, focusing the excitation light onto the spot that is roughly equivalent to a gel pad in size, so as to excite most of the label in an immobilization site simultaneously.

A novel feature of the biochip scanner device 100 is that the objective lens 121 used for both focusing the excitation beam and collecting the fluorescent signal is located in a miniature remote scanning head 118 linked to the rest of the optical path elements by the optical fiber 112. Accordingly, the fiber 112 is used for transmitting both the excitation beam and the fluorescence signal to and from the scanning head, respectively. This feature considerably simplifies the scanner design, because other optical path elements can be stationary. The fluorescence light emerging from the fiber 112 at the fiber holder 114 has a divergence much greater than that of the original laser beam. As a result, the diameter of the fluorescence beam after the collimating lens 110 is about 3 cm, which means that the small deflection mirror 108 used for coupling the excitation beam into the fiber 112 will block only a small fraction of the fluorescence flux.

After passing through the lens 110, the fluorescence beam passes through an emission interference filter 128 and an iris diaphragm 130. The emission interference filter 128 is a filter that rejects all light except fluorescent light. A second lens 132 is used to focus the filtered light onto a silicon photodiode 134 that is equipped with a low-noise pre-amplifier and supported by a positioner 136. The output of the photodiode pre-amplifier is further amplified and demodulated by a lock-in amplifier 138. The lock-in amplifier 138 is phase-locked to the chopper driver reference signal, to provide improved signal-to-noise ratio. The output of the lock-in amplifier 138 is a DC voltage that is proportional to the intensity of the fluorescence signal. The output of the lock-in amplifier 138 is digitized by an analog-to-digital converter (ADC) card 142 and then processed by a host computer 140.

The same lens part number PAC070 sold by Newport of Irvine, Calif. as used for lens 110 can be used for lens 132. A filter part number 645RDF72 sold by Omega Optical of Brattleboro, Vt. can be used for emission filter 128. Iris diaphragm 130 can be implemented with a part number M-ID-1.5 sold by Newport of Irvine, Calif. A photoreceiver model 2001 sold by New Focus of Santa Clara, Calif. can be used for PIN photodiode 134. A lock-in amplifier model 5105 sold by EG&G Instruments of Princeton, N.J. can be used for lock-in amplifier 138. The ADC card 142 can be implemented with a data acquisition card number PCI-MIO-16XE-50 sold by National Instruments of Austin, Tex. The scanning mechanics 126 can be implemented with X-Y scanning stage sold by Newport of Irvine, Calif.

Figure 2:
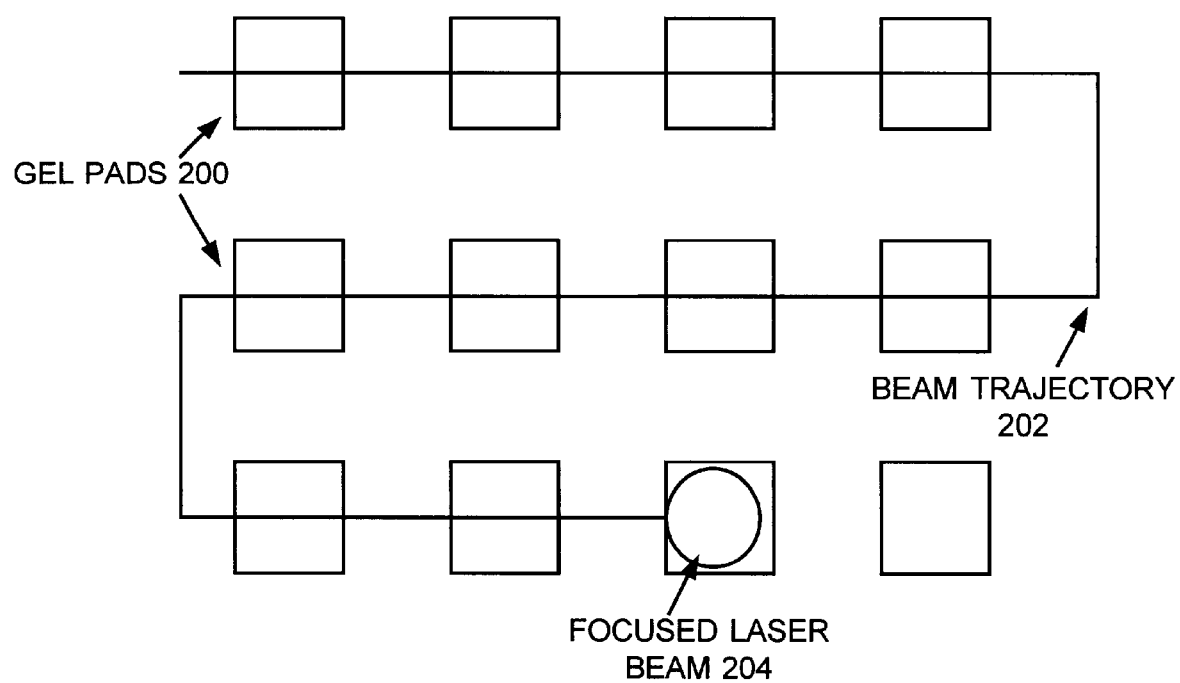
FIG. 2 is a diagram illustrating a method of scanning with the biochip scanner device in accordance with the preferred embodiment.

FIG. 2 illustrates a method of scanning with the biochip scanner device 100 in accordance with the preferred embodiment. An innovative method called Row Scanning (RS) is used with the biochip scanner device 100. In the RS method, a row of a biochip is scanned with a beam of a size that matches the immobilization site. An advantage of the RS method of the preferred embodiment where the length of time to accumulate the data is a consideration is that the RS method allows for real-time data processing, so that the integral signal intensities can be available for comparison and storage at the same rate that the chip 122 is being scanned. On the other hand, a reduction in scanning velocity can allow the sensitivity and dynamic range of the biochip scanner device 100 to be comparable with that of more expensive, conventional systems. Using the RS method provides a flexible and reliable way to relax hardware characteristics such as bandwidth, analog-to-digital conversion rate, optical resolution, and scanning mechanics parameters, depending upon the constraint of a particular user's needs, without sacrificing sensitivity and dynamic range of the biochip scanner device 100.

Figure 3:
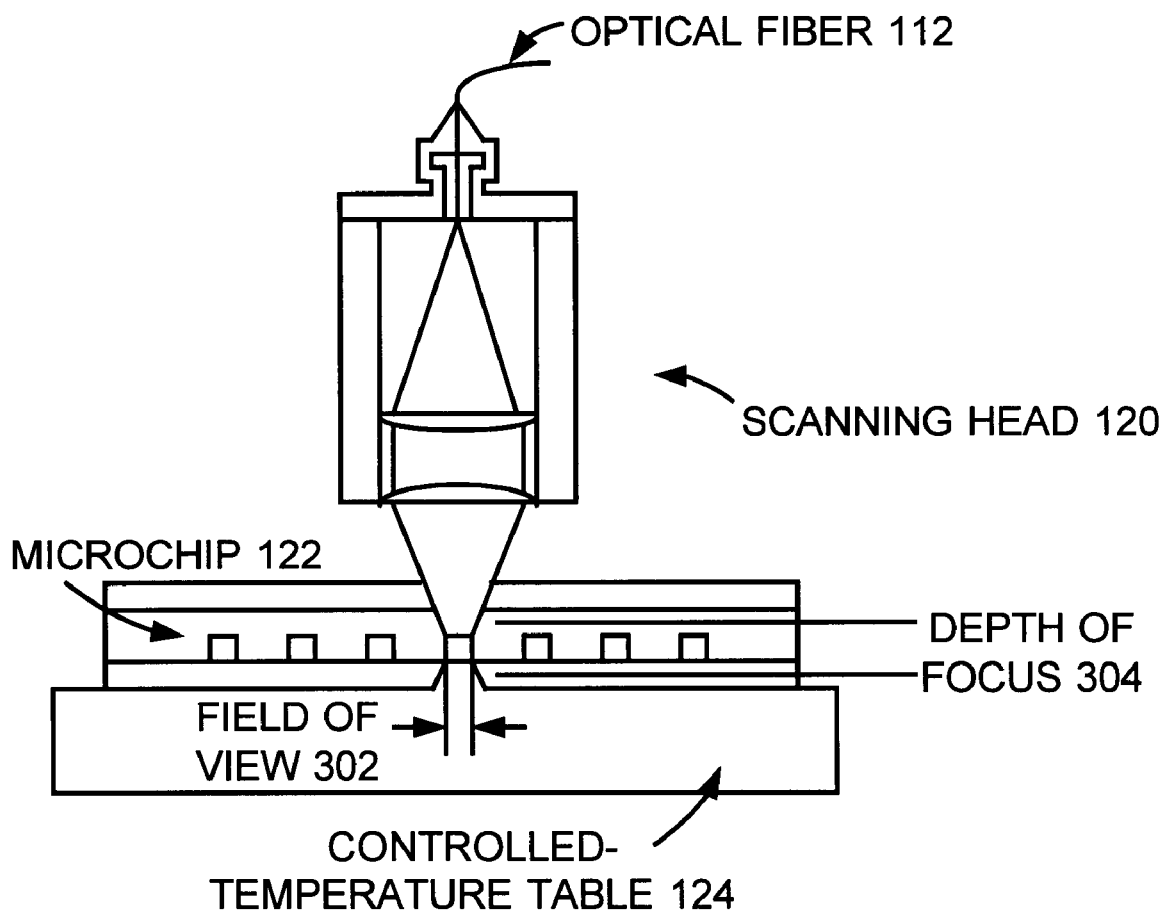
FIG. 3 is a diagram illustrating a field of view and depth of focus of a scanning head of the biochip scanner device in accordance with the preferred embodiment.

FIG. 3 illustrates a field of view 302 and a depth of focus 304 with the scanning head 118 of the biochip scanner device 100 in accordance with the preferred embodiment. Referring also to FIG. 2, the laser beam size substantially matches the gel pads 200 or immobilization site.

Figure 4B:
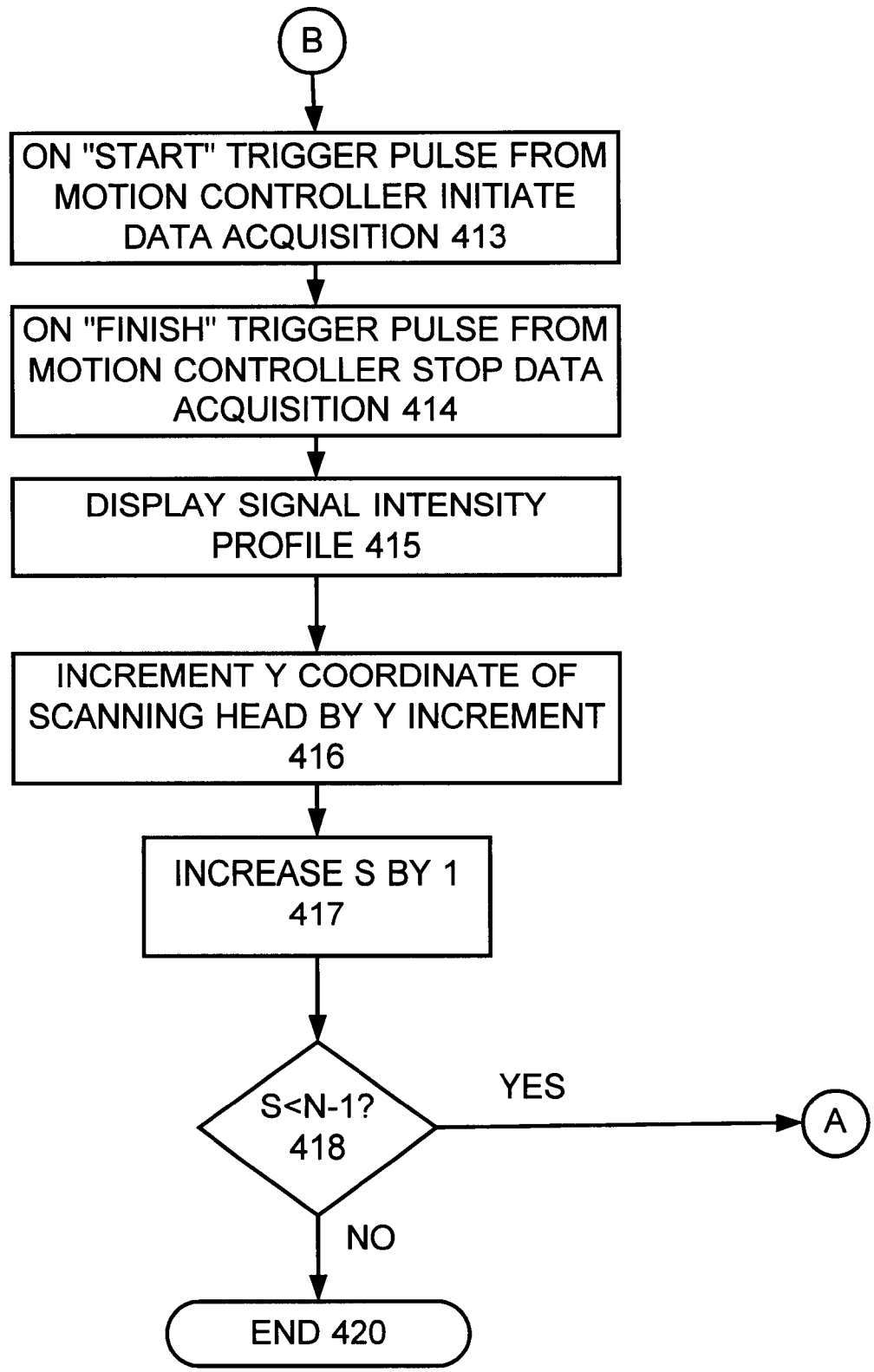

FIGS. 4A and 4B together provide a flow chart illustrating the Row Scanning (RS) method of the preferred embodiment starting at a block 401. The area to be scanned is limited to essentially the rows of the biochip array. Each row is scanned in a single pass of the laser beam while the laser beam size is matched to the immobilization site. At the same rate of the chip being scanned, the amplitudes of the fluorescence peaks are recorded. As a result, the amplitudes of the fluorescence peaks recorded give the integral signal intensities, which are most relevant to biochip applications. Since the scanner implementing the RS technique generates data that requires minimum, if any off-line processing, it is inherently suitable for high-rate data acquisition, which, in the same time, can be realized at slower scanning speeds. Or on the other hand, the reduction in scanning speed allows the sensitivity and dynamic range of the inexpensive biochip scanner device 100 to be comparable with that of more expensive, conventional systems.

An X scan amplitude as indicated in a block 402 is received from a user input at block 403. Other received user inputs include scan velocity, Y increment, number N of rows to scan and XY start point, respectively indicated at blocks 404, 405, 406, and 407. The scanning head 118 is brought to the start point as indicated in a block 408. Then counter S is cleared of scanned rows as indicated in a block 409. Checking whether S is even is performed as indicated in a decision block 410. When not even, the X scan is initiated in the "−" direction as indicated in a block 411. Otherwise, when even the X scan is initiated in the "+" direction as indicated in a block 412. Continuing with FIG. 2B following entry point B, on a start trigger pulse from the motion controller, data acquisition is initiated as indicated in a block 413. On a finish trigger pulse from the motion controller, data acquisition is stopped as indicated in a block 414. The signal intensity profile is displayed as indicated in a block 415. The Y coordinate of the scanning head is incremented by the Y increment as indicated in a block 416. S is increased by 1 as indicated in a block 416. Next X is compared to the number of rows to scan, S<N-1, as indicated in a decision block 418. When S is less than N-1, then the sequential operations return to decision block 410 in FIG. 4A. Otherwise, the sequential operations end as indicated in a block 420.

A practical evaluation of the biochip scanner device 100 of the preferred embodiment has shown that compact photodiodes 134 and low-power lasers 102 can provide the performance characteristics necessary for reliable detection of fluorescence at the level of 100,000 fluorescent molecules/gel pad. This sensitivity could be further improved by using a red and/or an infrared diode laser 102 as an excitation source. Assuming a 100 $\mu$m gel pad size, a 200 $\mu$m space between adjacent gel pads, biochip scanner device 100 can provide an effective acquisition rate of about 29 immobilization sites per second. This is an improvement over conventional systems.

While the present invention has been described with reference to the details of the embodiments of the invention shown in the drawing, these details are not intended to limit the scope of the invention as claimed in the appended claims.

What is claimed is:

1. A biochip scanner device, said biochip scanner device for quantifying a plurality of linear arrays of substantially separated, dimensionally uniform fluorescent targets, said arrays located at known positions on a plain support of a biochip; said biochip scanner device comprising:

a laser for emitting a laser beam of excitation radiation;

a modulator for modulating said laser beam;

a scanning head for receiving said modulated laser beam; said scanning head for focusing said laser beam of excitation radiation into a focal spot; said focal spot having a selected size substantially equal to a size of said substantially separated, dimensionally uniform fluorescent targets; and a scanning mechanics coupled to said scanning head for moving said scanning head relative to the biochip for directing said laser beam focal spot for sequentially illuminating said fluorescent targets one at a time; said laser beam focal spot causing substantially entire excitation of each said illuminated fluorescent target; and for sequentially collecting fluorescence of each said illuminated fluorescent target.

2. A biochip scanner device as recited in claim 1 wherein said scanning head includes an objective lens for focusing said modulated laser beam into said focal spot.

3. A biochip scanner device as recited in claim 2 wherein said scanning head for sequentially collecting fluorescence of each said illuminated fluorescent target has a field of view substantially equal to size of said fluorescent target.

4. A biochip scanner device as recited in claim 1 includes an optical fiber delivering said modulated laser beam to said scanning head and collecting said fluorescence from said scanning head for each said illuminated fluorescent target.

5. A biochip scanner device as recited in claim 1 includes an emission interference filter coupled to said scanning head for receiving and filtering said fluorescence from each said illuminated fluorescent target.

6. A biochip scanner device as recited in claim 1 includes a photodiode for detecting said fluorescence from each said illuminated fluorescent target.

7. A biochip scanner device as recited in claim 1 includes a single-element photodetector for detecting said fluorescence from each said illuminated fluorescent target.

8. A biochip scanner device as recited in claim 7 wherein said single-element photodetector includes a preamplifier and further includes a lock-in amplifier coupled to said photodetector, said lock-in amplifier for amplifying a photodetector signal at a modulating frequency of said modulator.

9. A biochip scanner device as recited in claim 8 wherein said lock-in amplifier provides a DC signal proportional to an intensity of said fluorescence; and includes an analog-to-digital converter (ADC) for digitizing said DC signal; and a computer for processing said digitized DC signal.

10. A biochip scanner device as recited in claim 1 wherein said laser includes a low-power He—Ne laser and wherein said modulator includes an optical chopper.

11. A biochip scanner device as recited in claim 1 wherein said laser includes one of a red or infrared diode laser and wherein said modulator includes a current driver providing a periodic train of current pulses with a period corresponding to a desired modulation frequency.

12. A method of using a biochip scanner device, said biochip scanner device for quantifying a plurality of linear arrays of substantially separated, dimensionally uniform fluorescent targets, said arrays located at known positions on a plain support of a biochip; said method comprising the steps of:

defining a number of linear segments for scanning; at least some of said segments passing along a number of said linear arrays of fluorescent targets;

focusing a laser beam of excitation radiation into a focal spot; said laser beam focal spot substantially matching a size of said fluorescent targets; and sequentially scanning each of said defined linear segments; directing said laser beam focal spot and sequentially illuminating predefined ones of said fluorescent targets one at a time within each of said defined linear segments; said laser beam focal spot causing substantially entire excitation of each said illuminated fluorescent target;

sequentially collecting fluorescence of each said illuminated fluorescent target and quantifying an intensity of said collected fluorescence of each said illuminated fluorescent target; and recording said fluorescence intensity of each said illuminated fluorescent target.

13. A method as recited in claim 12 includes the step of digitizing said fluorescence intensity utilizing an analog-to-digital converter; and processing said digitized DC signal utilizing a computer.

14. A method as recited in claim 13 wherein the step of sequentially collecting fluorescence of each said illuminated fluorescent target and quantifying an intensity of fluorescence of each said illuminated fluorescent target includes the steps of coupling said collected fluorescence of each said illuminated fluorescent target to a photodiode and amplifying a photodiode signal with a lock-in amplifier at a modulating frequency of a modulator for quantifying said intensity of fluorescence of each said illuminated fluorescent target.

15. A method as recited in claim 12 wherein the step of sequentially scanning each of said defined linear segments includes the step of providing a scanning head coupled to an optical fiber for receiving a modulated laser beam; utilizing said scanning head for focusing a laser beam of excitation radiation into a focal spot, said laser beam focal spot substantially matching a size of said fluorescent targets; directing said laser beam focal spot and sequentially illuminating predefined ones of said fluorescent targets one at a time within each of said defined linear segments; said laser beam focal spot causing substantially entire excitation of each said illuminated fluorescent target; and said scanning head for transmitting said collected fluorescence peaks to said optical fiber.

16. A biochip scanner device, said biochip scanner device for quantifying a plurality of linear arrays of substantially separated, dimensionally uniform fluorescent targets, said arrays located at known positions on a plain support of a biochip; said biochip scanner device comprising:

a laser for emitting a laser beam of excitation radiation;

a modulator for modulating said laser beam;

a scanning head for receiving said modulated laser beam; said scanning head for focusing said laser beam of excitation radiation into a focal spot; said focal spot having a selected size substantially equal to a size of each said substantially separated, dimensionally uniform fluorescent targets;

a scanning mechanics coupled to said scanning head for moving said scanning head relative to the biochip for directing said laser beam focal spot for sequentially illuminating said fluorescent targets one at a time; said laser beam focal spot causing substantially entire excitation of each said illuminated fluorescent target; and for sequentially collecting fluorescence of each said illuminated fluorescent target;

a photodetector for detecting said collected fluorescence of each said illuminated fluorescent target from the biochip; and an optical fiber for delivering said modulated laser beam to said scanning head and said optical fiber for delivering said collected fluorescence of each said illuminated fluorescent target to said photodetector.

17. A biochip scanner device as recited in claim 16 further includes an emission interference filter coupled to said optical fiber for filtering said collected fluorescence of each said illuminated fluorescent target.

18. A biochip scanner device as recited in claim 16 wherein said modulator includes an optical chopper and wherein said photodetector includes a photodiode and a lock-in amplifier for amplifying a photodiode signal at a modulating frequency of said optical chopper.

19. A biochip scanner device as recited in claim 18 wherein said lock-in amplifier provides a DC signal proportional to an intensity of said collected fluorescence of each said illuminated fluorescent target.

20. A biochip scanner device as recited in claim 16 wherein said scanning head includes an objective lens for focusing said modulated laser beam of excitation radiation into a focal spot and for collecting said fluorescence of each said illuminated fluorescent target.

* * * * *